United States Patent [19]

Kamoun et al.

[11] Patent Number: 5,173,491
[45] Date of Patent: Dec. 22, 1992

[54] PHARMACEUTICAL COMPOSITIONS AND A METHOD FOR THE TREATMENT OF MEMORY DISORDERS, INTELLECTUAL DISORDERS OF AGEING AND ALZHEIMER'S DISEASE

[75] Inventors: Annie Kamoun; Elisabeth Mocaer, both of Neuilly sur Seine; Gilbert Regnier, Chatenay Malabry; Claude Guillonneau, Clamart; Jacques Duhault, Croissy sur Seine, all of France

[73] Assignee: Adir et Compagnie, Courbevoie, France

[21] Appl. No.: 585,615

[22] Filed: Sep. 20, 1990

[30] Foreign Application Priority Data

Aug. 10, 1990 [FR] France ................. 90 10235

[51] Int. Cl.$^5$ ............................ A01N 43/90
[52] U.S. Cl. ........................... 514/265; 514/267; 514/269
[58] Field of Search ............... 514/265, 227, 232.2, 514/234.2, 267, 266, 258

[56] References Cited

U.S. PATENT DOCUMENTS

| 4,599,338 | 7/1986 | Regnier et al. | 514/234.2 |
| 4,783,530 | 11/1988 | Rzeszotarski et al. | 544/267 |
| 4,956,363 | 9/1990 | Wülfert et al. | 514/232.2 |

Primary Examiner—Frederick E. Waddell
Assistant Examiner—T. J. Criares
Attorney, Agent, or Firm—Gordon W. Hueschen

[57] ABSTRACT

1,3,7-trimethyl-8-[3-(4-diethylaminocarbonylpiperazino) propyl] xanthine and physiologically tolerable acid addition salts thereof may be used for the preparation of medicaments for the treatment of memory disorders, intellectual disorders of ageing, and Alzheimer's disease.

2 Claims, No Drawings

PHARMACEUTICAL COMPOSITIONS AND A METHOD FOR THE TREATMENT OF MEMORY DISORDERS, INTELLECTUAL DISORDERS OF AGEING AND ALZHEIMER'S DISEASE

The present invention provides the use of a derivative of 1,3,7-trimethylxanthine for the preparation of medicaments for the treatment of memory disorders, intellectual disorders of ageing, and Alzheimer's disease.

More specifically, the invention provides the use of 1,3,7-trimethyl-8-[3-(4-diethylaminocarbonyl-piperazino)propyl] xanthine and of its physiologically tolerable acid addition salts for the preparation of medicaments for the treatment of memory disorders, intellectual disorders of ageing, and Alzheimer's disease.

1,3,7-trimethyl-8-[3-(4-diethylaminocarbonyl-piperazino) propyl] xanthine and its physiologically tolerable acidaddition salts are described in U.S. Pat. No. 4,599,338 as being able to be used in the treatment of migraine and asthenia, at a dosage of 50 mg/kg p.o., by reason of their analgesic properties on the one hand and psychotonic properties on the other hand.

The Applicant has now discovered that 1,3,7-trimethyl-8-[3-(4-diethylaminocarbonylpiperazino) propyl] xanthine and its physiologically tolerable acid addition salts have interesting properties, in particular properties facilitating memory acquisition and retention, and antiamnesic properties which make it possible for them to be used for the preparation of medicaments for the treatment of memory disorders, intellectual disorders of ageing, and Alzheimer's disease, and this at specific dosages very much lower than the dosages used previously for the treatment of migraine.

A further object of the present invention is pharmaceutical compositions containing as active ingredient 1,3,7-trimethyl-8-[3-(4-diethylaminocarbonyl-piperazino)propyl] xanthine or one of its physiologically tolerable salts, in admixture or association with a suitable pharmaceutical excipient.

The pharmaceutical compositions thus obtained are advantageously presented in pharmaceutical forms suitable for oral or parenteral administration, and especially intravenous administration, such as, for example, tablets, dragees, gelatin-coated pills, and injectable or drinkable solutions. The pharmaceutical compositions according to the present invention are characterized in that they contain 2 to 50 mg of active ingredient, in admixture or association with a suitable pharmaceutical excipient.

The posology varies according to the age and weight of the patient, the method of administration, the nature of the therapeutic indication and of associated treatments, and ranges between 2 and 50 mg of active ingredient per dose from 1 to 3 times a day.

The following Examples illustrate the invention and do not limit the latter in any way.

All the tests which follow were carried out using as active ingredient (in particular owing to its good aqueous solubility) 1,3,7-trimethyl-8-[3-(4-diethylaminocarbonylpiperazino) propyl] xanthine hydrochloride of formula I :

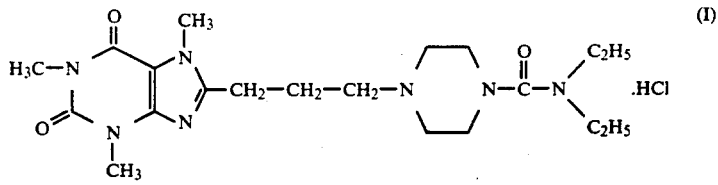

EXAMPLE 1

EFFECT OF PRODUCT I ON THE SPEED OF ACQUISITION AND LEARNING

The procedure used, described by GALEY, DURKIN, SIFAKIS, KEMPF and JAFFARD in Brain Res., 340, 171-174 (1985), makes it possible to:
1) Measure spontaneous alternation, the modifications of which often predict the effects of a treatment on learning and spatial memory.
2) Measure the speed of acquisition of a simple spatial discrimination (right-left) that a normal animal masters in about twenty attempts.
3) Evaluate memory retention of this discrimination during a trial carried out 24 hours later.

(A) TECHNIQUES AND METHODS

Animals

Fifty male mice of the BALB/c strain, never before exposed to experimentation and aged from 12 to 14 weeks, were used. They were kept in individual cages in an air-conditioned animal laboratory (22° C.) and provided with an artificial light/dark cycle of 12 hours (0800-2000 hours).

Apparatus

This is a T-shaped labyrinth made of grey Plexiglas. The central corridor and the two arrival arms measure 35 cm long, 10 cm wide and 25 cm high. The departure compartment (10×12 cm) is separated from the central corridor by a guillotine gate. The entry to each arm is also provided with a gate.

Procedure

Familiarisation: The actual experiment is preceded by 2 familiarisation sessions of 10 min. (free exploration; 1 session per day).

Spontaneous alternations and acquisition of spatial discrimination : These two trials take place on the following day, without interruption. During the first 6 attempts, food is aranged at the end of the two arms. During each attempt, the animal is placed in the departure compartment for 30 seconds (interval between attempts). The gate giving access to the central corridor is opened and the animal can choose between the two arms where it remains enclosed for 30 seconds. It is found that the normal animal alternates its successive choices (approx. 65% of alternation). Starting from the 7th attempt, food is placed only in a single arm, always the same one. The trial continues until the animal successfully completes 5 attempts in a row without error (that is to say, goes 5 times into the filled arm : criterion).

Retention of spatial discrimination : This takes place under the same conditions as acquisition, after a period of 24 hours. The trial continues until the animal again reaches the criterion of 5 out of 5.

Groups

The 50 animals were divided into 5 groups of 10 subjects :
- control-control (no treatment)
- solvent-solvent (0.1 ml/10g of 7% NaCl under the same conditions)
- drug-drug (injection of product I, 30 min. before each trial : 0.0625–0.25–1 mg.kg$^{-1}$ administered intraperitoneally).

B) RESULTS

1) Spontaneous Alternations

The results of the 5 groups are summarised in FIG. A. The minimum dose (D1:0.0625 mg.kg.$^{-1}$) improves the percentage of alternations (from 59.0+3.1% to 72.0 +5.3%).

2) Acquisition of Spatial Discrimination

The results are summarised in FIG. 8. It is found that the administration of product I at a dosage of 0.0625 mg.kg.$^{-1}$ (D1) very significantly reduces the number of attempts to the criterion. Product I improves the speed of acquisition in a dose-dependent manner, the dose D1 giving a higher speed of acquisition than the dose D2 and the dose D3.

3) Retention of Spatial Discrimination

The results are summarised in FIG. C. At the dosage of 0.0625 mg.kg$^{-1}$, the product very significantly reduces the number of attempts to the criterion; this is not the case for higher dosages. There again, there is a dose-dependent facilitating effect, the dose D1 causing the criterion to be reached significantly more rapidly than D2 and D3.

4) Conclusion

The administration i.p. of Product I, 30 mins. before each trial, improves spontaneous alternation, acquisition and retention, 24 hours later, of spatial discrimination ( trials carried out in the T-shaped labyrinth). These facilitations are observed at the lowest dosage used in the procedure (0.0625 mg.kg$^{-1}$) and not at the two higher dosages (0.025 and 1 mg.kg$^{-1}$).

5) Graphic Expression of Results

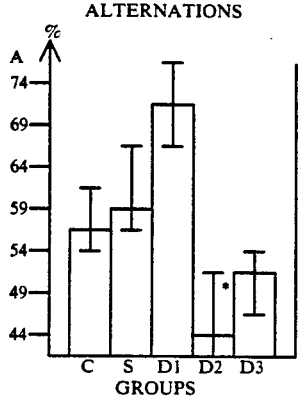

FIG. A: Spontaneous alternations (mean ± SD)
ALTERNATIONS

C: control
S: solvent
D1: 0.0625 mg · kg$^{-1}$
D2: 0.25 mg · kg$^{-1}$
D3: 1.0 mg · kg$^{-1}$
*significantly different from C + S; p <0.05

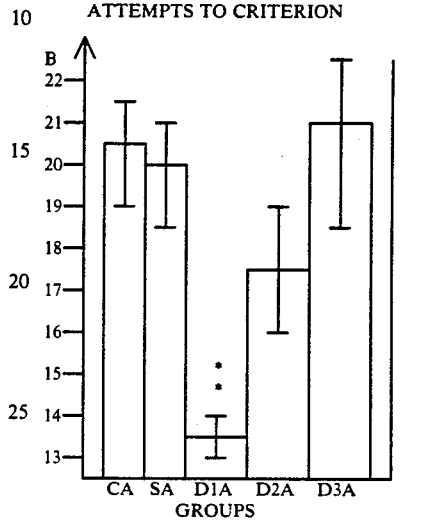

FIG. B Acqusition of discrimination
(attempts to criterion: mean ± SD)
ATTEMPTS TO CRITERION

**significantly different from C and S; p <0.001

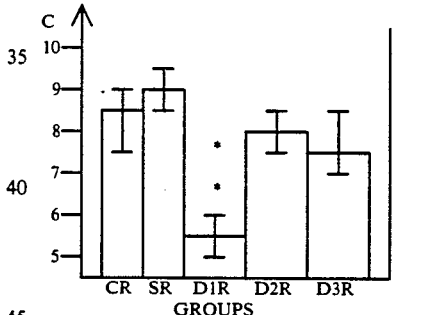

FIG. C: Retention of discrimination (cf. FIG. B)
ATTEMPTS TO CRITERION

**significantly different from C and S; p < 0.001

EXAMPLE 2

Effect of Product I on Retention of the Memory Phenomenon

1) Study of Passive Avoidance Conditioning in Rats

A) Methodology :

In this test, the rats can explore freely for 5 minutes a large white compartment and a small black compartment. The time spent in each zone is noted, and also the amount of time taken by the rats released into the white compartment to pass for the first time into the black compartment. Each rat is then trapped in the black compartment and receives an electric shock to the paws which is impossible to avoid. A minute later, the rat undergoes another 5 minute attempt in which it is free to go into the white or the black compartment. The time taken before passing into the black compartment and the duration of the stay in the latter are noted. The memory fixation of this passive avoidance response is then tested in all the rats after 48 hours.

The following dosages of Product I (expressed as base) were tested : 0.0625, 0.25, 1 and 4 mg/kg. The control rats received distilled water; all the injections were administered intraperitoneally 30 minutes before the acquisition sessions and the tests for memory fixation after 48 hours. Ten rats were tested for each dosage.

B) Results

If the time taken before passing into the black compartment is considered, it can be seen that the control animals had no fixation during the test carried out 48 hours later. However, the groups of animals taken as a whole showed memory fixation.

If the data for all the groups are analysed, the animals spend significantly less time on the black side after 48 hours, compared with the situation before the shock, but the product x attempt interaction is of marginal significance. When only the data of the controls and of the 0.0625 mg/kg group are analysed, the product x attempt interaction reaches statistical significance. 2) Working and Reference Memory A) Methodology :

In this test, the rats were not deprived of food, since they were rewarded by a sugary titbit. Before the start of training, the rats received such titbits in their cages for five days in order to get them accustomed to them.

In each attempt, the sugary titbits were placed opposite 3 holes out of 9 possible holes; the task for the rat was to visit only the holes with titbits, to take and eat the latter, and not to return to the hole once the titbit had been taken from there. It was the same holes which received the bait each day, so that the visits to the holes without bait indicate errors of reference memory. Further visits to a hole where the titbit had already been removed and consumed indicate an error of the working memory in this study. The performances are analysed by the time taken to finish the task to be carried out (remove and consume the three titbits) and by the number and nature of the errors made. One attempt was carried out per day. When the animals had met the criterion (carrying out the task in less than 60 seconds, taking and eating the three sugary titbits and not committing more than one error), they were left quiet in their cages before undergoing a further test 7 days later. The memory fixation was tested three weeks later.

Male Lister rats were used; ten of them were assigned to each of the following groups : control (water); Product I (0.0625, 0.25, 1 and 4 mg/kg; all dosages expressed as base). The injections were administered intraperitoneally each day, 30 minutes before the test.

B) Results

All the animals learned to carry out the task. On the whole, Product I did not significantly change the time required to perform the task.

On the whole, the rats took significantly more time to perform the task when they were tested again after an interval of 7 days.

Product I had no overall effect on the number errors committed.

The groups had differences in the total number of errors committed on day 7. In this case, the 0.0625 mg/kg group committed significantly fewer total errors than the control group. If the different types of error made in this memory fixation test are analysed, it is found that the 0.0625 mg/kg group committed fewer errors of each type, and that the difference for errors of reference memory is close to statistical significance.

3) Conclusion

The tasks selected for this study measure different types of learning. It is clear that Product I has no effect on habituation in the long term, even when a long delay of 48 hours is used between the attempts.

In the learning task with reward, Product I had a tendency (in particular at the lowest dosage) to hinder acquisition. However, in the test for memory fixation after a week, the lowest dose (0.0625 mg/kg) significantly reduced the number of errors committed (in particular errors of reference memory), which indicates an improvement in the long term memory fixation of this task. The same dosage improved the long term (48 hours) fixation of the passive avoidance response. It may therefore be concluded that Product I improves long term memory fixation of rewarded or punished tasks.

EXAMPLE 3

Anti-Amnesic Action of Product I

1) Effects of Product I on Amnesia Induced by Scopolamine in the Pasive Avoidance Test in Mice A) Methodology :

The test was carried out on male mice of the N.M.R.I. strain, having an average weight per group of 24 to 27 g. The compounds used were :
product I, in solution in distilled water;
piracetam (reference product) in solution in distilled water;
scopolamine hydrobromide in solution in a 0.9% solution of NaCl.

All the attempts were carried out at ambient temperature (20°-21° C.) in artificial light.

The test, according to the technique of LENEGRE A. et al., Pharmacol. Biochem.Behar., 29, 625-629 (1988), was carried out as follows:

A mouse is introduced into the illuminated compartment (10×10×29 cm) of a box with two compartments. When it has passed with all four paws through the passage giving access to the dark compartment of larger size (19.5 ×16.5×29 cm), it receives a slight electric shock (0.35 mA) until it returns to the illuminated compartment, from which it is immediately removed (S1). When the mouse is reintroduced 24 hours later into the system (S2), it avoids entering the dark compartment. The time taken to pass into the latter is measured, up to 180 seconds.

An injection i.p. of scopolamine (1 mg/kg) 30 minutes before S1 reduces the memory, this being measured by the time taken by the mouse to pass into the dark compartment at the session S2.

This amnesia is reduced by nootropic agents such as piracetam, cf. SCHINDLER U. et al, Drug Dev. Res., 4, 567-576, (1984). 18 animals are studied in each group. The experiment is carried out blind.

Product I was studied at the following dosages : 0.25, 1.4 and 16 mg/kg (first experiment) and 0.0625, 0.125, 0.25 and 0.5 mg/kg (second experiment), administered per os 60 minutes before S1.

Piracetam (2048 mg/kg p.o.), administered under the same experimental conditions, was used as reference compound in the two experiments.

B) Results

Under the experimental conditions, product I at dosages ranging between 0.0625 and 0.5 mg/kg significantly antagonised the amnesia induced by the scopolamine. At higher dosages (1.4 and 16 mg/kg) no significant effect was observed. According to these results, it may therefore be concluded that product I has an anti-amnesic activity over a wide range of dosages.

2) Effects of Product I on Amnesia Induced by Diazepam Electric Shock in the Passive Avoidance Test in Mice

A) Methodology

The operating conditions and the test used are identical to those described above [cf. 1)-A], but here amnesia is induced not by scopolamine but by:
either diazepam used in dispersion in a 5% suspension of gum arabic,
in which case:
An injection i.p. of diazepam (1 mg/kg) 30 minutes before S1 reduces the memory, this being measured by the time taken by the mouse to pass into the dark compartment at session S2. This amnesia is reduced by nootropic agents such as piracetam, cf. SCHINDLER U., Drug Dev. Res., 4, 567–576, (1984).
18 animals are studied in each group. The experiment is carried out blind.
Product I was studied in the following dosages 0.0312, 0.0625, 0.125 and 0.25 mg/kg, administered per os 60 minutes before S1.
Piracetam (2048 mg/kg p.o.), administered under the same experimental conditions, was used as reference compound.
or by electric shock,
in which case:
An electric shock (square-wave current, 0.4 sec., 50 mA, 50 Hz, by means of temporal electrodes connected to an Ugo Basile shock generator) administered immediately after S1 reduces the memory, this being measured by the time taken by the mouse to pass into the dark compartment at session S2. This amnesia is reduced by nootropic agents such as piracetam, cf. BANFI et al., J. Pharmacol. Meth., 8, 255–263, (1982).
18 animals are studied in each group. The experiment is carried out blind.
Product I was studied at the following dosages 0.0312, 0.0625, 0.125 and 0.25 mg/kg, administered per os 60 minutes before S1.
Piracetam (2048 mg/kg p.o.), administered under the same experimental conditions, was used as reference compound.

B) Results

Under the above operating conditions, product I:
antagonised in a dose-dependent manner the amnesia-producing effects of the diazepam, with an antagonism of 97% for the strongest dosage tested (0.25 mg/kg);
did not antagonise the amnesia-producing effects of the electric shock, whatever the dosage.
Piracetam (2048 mg/kg per os), under the same experimental conditions, antagonised the amnesia-producing effects of the diazepam by 89% and those of the electric shock by 83%.

3) Effects of Single and Repeated Administration of Product I on Amnesia Induced by Scopolamine in the Passive Avoidance Test in Mice

A) Methodology:

This test, which shows the effects of product I in acute treatment on the one hand and in chronic treatment on the other, was carried out on male mice of the N.M.R.I. strain having an average weight per group of 25 to 26 g.
The operating conditions and the test used are identical to those previously described (cf. 1/-A).
The dosages of product I studied were:
Single administration: 0.0312 mg/kg, administered 60 minutes before the learning attempt (S1) on day A. From day 1 to day 3 the animals received distilled water twice a day (at 0900 and 1600 hours).
Repeated administration: 0.0312 and 0.25 mg/kg, administered twice a day (at 0900 and 1600 hours) for three days and 60 minutes before S1 on day 4.
Piracetam (2048 mg/kg), administered only once under the same experimental conditions, was used as reference compound.

B) Results

Under the above experimental conditions, product I, administered only once at the two dosages tested, clearly antagonised the amnesia induced by scopolamine (antagonism 87% at a dosage of 0.0312 mg/kg and 91% at 0.25 mg/kg).
Repeated administration of the same dosages over a period of four days resulted in a more marked antagonism of the amnesia induced by scopolamine, under the same experimental conditions (93% and 106% respectively). The difference between single administration and repeated administration was significant at a dosage of 0.25 mg/kg.
According to these results, it may be concluded that the repeated administration of product I:
induces no exhaustion of the anti-amnesic effects observed after single administration,
potentiates its anti-amnesic effects.
However, since the antagonism of amnesia after repeated administration at the lowest dose was not maximum and remained lower than that obtained with the reference compound (piracetam), this potentiation is not very marked.

4) Study of Specificity of the Anti-Amnesic Effect of Product I

In addition to the tests described above, product I was studied after oral administration to male mice of the N.M.R.I. strain in order to evaluate any possible interaction with the effects of scopolamine (1 mg/kg i.p.) on spontaneous locomotor activity and with the effects of diazepam (1 mg/kg i.p.) in the four-plate test (anxiolytic activity).
The dosage used was 0.25 mg/kg, administered 60 minutes before the tests (i.e. 30 minutes before the injection i.p. of scopolamine or diazepam). This is the strongest dosage of product I which antagonised the amnesia induced by scopolamine or diazepam in the passive avoidance test (1, 2).
The results obtained show:
the absence of antagonism of hypermotility induced by scopolamine in activity/metre;

absence of antagonism of unblocking, induced by diazepam, of the behaviour punished in the four-plate test.

These results confirm that the anti-amnesic effects of product I are not linked to the specific nature of these two amnesia-inducing agents, and make it possible to conclude the specificity of the anti-amnesic action of product I at a low dosage.

We claim:

1. A method for treating a human being afflicted with a memory disorder, an intellectual disorder of ageing or Alzheimer's disease, which consists in administering to the said human being an effective amount of 1,3,7-trimethyl-8-[3-(4-diethylaminocarbonylpiperazino)propyl] xanthine or one of its physiologically-tolerable acid addition salts, said effective amount being from about 2 to 50 mg per dose.

2. The method of claim 1, wherein the xanthine compound is administered in the form of its hydrochloride salt.

* * * * *

UNITED STATES PATENT AND TRADEMARK OFFICE
CERTIFICATE OF CORRECTION

PATENT NO. : 5,173,491

DATED : Dec. 22, 1992

INVENTOR(S) : Annie Kamoun, Elisabeth Mocaer, Gilbert Regnier, Claude Guillonneau, Jacques Duhault It is certified that error appears in the above-identified patent and that said Letters Patent is hereby corrected as shown below:

Column 3, approximately line 21; "59.0+" should read --59.0±--.
Column 3, approximately line 22; "+5.3%)." should read -- ± 5.3%). --.
Column 4, approximately line 39, "Fig C", last two columns; reads " 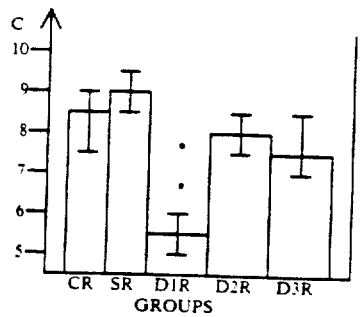 " should read -- 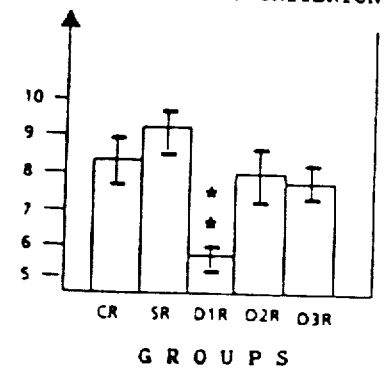 --.

Signed and Sealed this

Twenty-first Day of December, 1993

Attest:

BRUCE LEHMAN

Attesting Officer   Commissioner of Patents and Trademarks